United States Patent
Danel

[11] 3,983,740
[45] Oct. 5, 1976

[54] METHOD AND APPARATUS FOR FORMING A STREAM OF IDENTICAL DROPS AT VERY HIGH SPEED

[75] Inventor: François Danel, Uriage, France

[73] Assignee: Societe Grenobloise d'Etudes et d'Applications Hydrauliques (Sogreah), France

[22] Filed: Feb. 7, 1975

[21] Appl. No.: 548,097

Related U.S. Application Data

[63] Continuation-in-part of Ser. No. 312,892, Dec. 7, 1972, abandoned.

[30] Foreign Application Priority Data

Dec. 7, 1971   France ............................... 71.44960

[52] U.S. Cl. ..................................... 73/12; 83/177
[51] Int. Cl.² ............................................ G01N 3/32
[58] Field of Search ................ 73/11, 12, 86; 239/4, 239/101, 102; 346/75; 83/177; 222/420

[56] References Cited
UNITED STATES PATENTS

| | | | |
|---|---|---|---|
| 2,512,743 | 6/1950 | Hansell | 73/71.5 U |
| 3,233,449 | 2/1966 | Harmon | 73/67.8 S |
| 3,237,623 | 3/1966 | Gordon | 73/67.8 |
| 3,281,860 | 10/1966 | Adams et al. | 346/75 |
| 3,373,752 | 3/1968 | Inoue | 239/4 |
| 3,380,584 | 4/1968 | Fulwyler | 346/75 |
| 3,823,408 | 7/1974 | Gordon | 346/75 |

Primary Examiner—James J. Gill
Assistant Examiner—Anthony V. Ciarlante
Attorney, Agent, or Firm—Craig & Antonelli

[57] ABSTRACT

A method and apparatus for producing a very fast succession of identical and well-defined drops, driven at very high speed, in which a jet of liquid which is divided into droplets by high-frequency vibration is produced at very high speed.

24 Claims, 7 Drawing Figures

METHOD AND APPARATUS FOR FORMING A STREAM OF IDENTICAL DROPS AT VERY HIGH SPEED

This application is a continuation-in-part application of my copending application Ser. No. 312,892, filed Dec. 7, 1972, now abandoned.

The present invention concerns a method and a device for cleaning, cutting and drilling holes in various substances, and also for studying rapidly and in a comparative way the reaction and characteristics of several samples of substances subjected to erosion by drops, such as radomes, helicopter rotor blades and turbine blades.

The method which is the object of the invention consists essentially in the producing of a high-speed jet of liquid, divided into droplets before being scattered by high-frequency vibrations concentrated in a judiciously chosen place.

A device for implementing the method consists in using a chamber for putting the liquid under very high pressure, ended by an injector having a suitable form to obtain a fast and high-quality jet over a length equal to a certain number of times its diameter. The discharge supply flows into the chamber. An ultrasonic generator having a judicious shape enables a high-frequency field to be made to converge at a given point at the level of the origin of the jet producing the high-frequency vibration which divides the latter into droplets.

In a variation of an embodiment, the high-frequency vibration is produced at the level of the origin of the jet by means of a magnetostrictive element situated at that place.

The premature disintegration of the jet of droplets may be avoided by a concentric jet of air or by a gas having the same speed as the drops.

In order to apply the method to the studying of the reaction of a sample subjected to the impact of drops thus produced, the jet of air is directed towards the sample placed in a container in which a vacuum is produced in order to have only the vapor pressure of the liquid used for reducing considerably the aerodynamic braking effect.

The maximum efficiency of the jet corresponds to fragmentation lengths of the jet equal to the diameter of the output nozzle.

To obtain such fragmentation, for a given speed of the jet, the frequency of the pulses must be inversely proportional to the diameter of the output nozzle.

These and other features, objects and advantages of the present invention will become more readily apparent from a consideration of the included specification and drawings wherein:

DETAILED DESCRIPTION OF THE INVENTION

Figure 1:
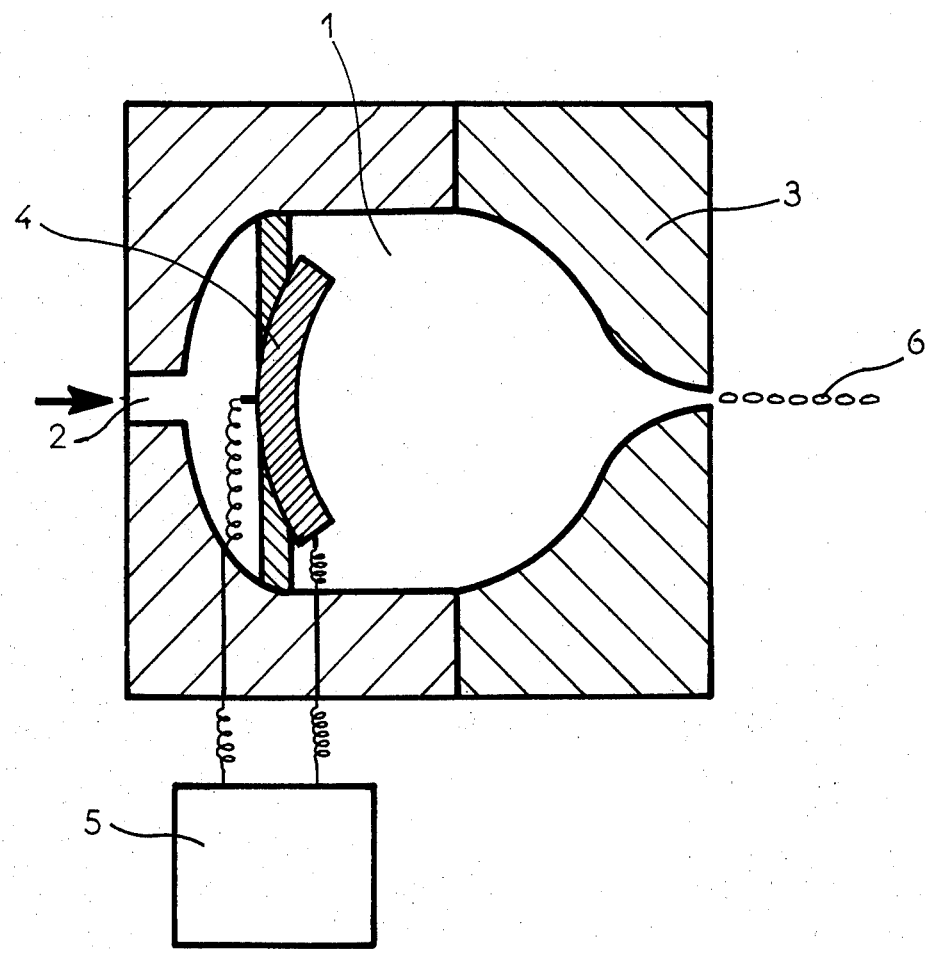
FIG. 1 is an axial cross-sectional view of a device according to the invention.

The device in FIG. 1 comprises a chamber 1 supplied with liquid under high pressure by a pump connected to the orifice 2, that chamber ending in an interchangeable injector 3 intended for providing a fast jet.

The orifice 2 of chamber 1 can be either a single inlet or plural inlets, but should be parallel to the longitudinal axis of the chamber as depicted in the figure in order to avoid turbulence in chamber 1 such as that caused by rotation of the liquid therein, and to enable proper control of a coherent jet of droplets. Orifice 2 being parallel to the longitudinal axis of chamber 1, avoids both rotation of liquid in the chamber and the production of an uncontrollable spiral jet of droplets of uncontrollable size which might otherwise immediately disintegrate.

An ultrasonic device 4 supplied by a high-frequency generator 5 supplies an ultrasonic field, whose frequency is chosen as a function of the dimension of the drops which are to be obtained and focusses that field at a point chosen close to the narrow portion of the injector.

The jet coming from the output orifice of the injector 3 in droplets 6 whose dimensions depend on the frequency of the generator 5 are thus divided.

For example, with a 1-mm injector nozzle diameter and an initial jet speed of 200 m/s, drops of 1 mm may be obtained with a frequency of 200 Kc/s.

The invention operates with the liquid in chamber 1 being under high pressure, the jet of droplets 6 emerging from the chamber with high velocity in the range of 100 meters/second at 750 psi in the chamber to 600 meters/second at 3000 psi in the chamber. It should be appreciated, therefore, that the pressures employed in the device are quite high considering, for example, that normal atmospheric pressure is approximately 14.7 psi.

This device enables cleaning, cutting, and drilling of various substances.

Premature disintegration of the jet may be avoided by a concentric jet of air or of a gas having the same speed as the drops.

Figure 2:
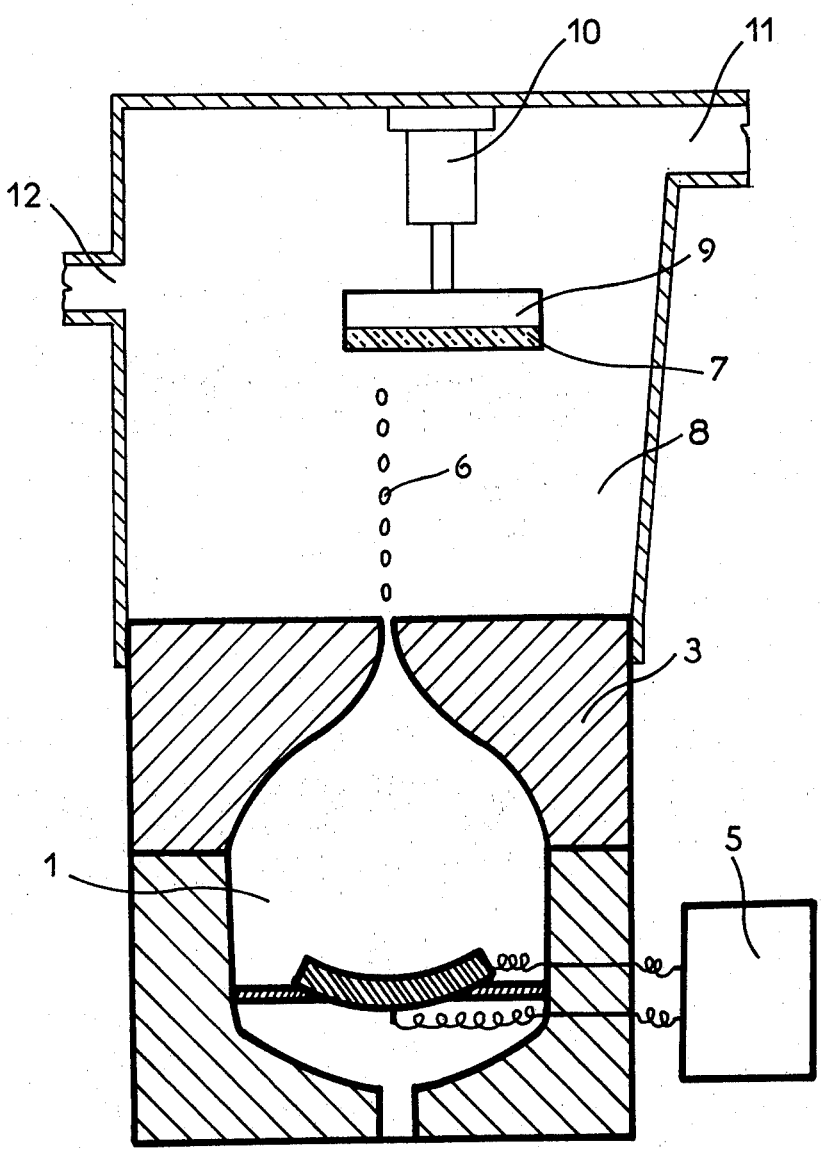
FIG. 2 is an axial cross-sectional view of the device depicted in FIG. 1, arranged for studying a sample.

FIG. 2 shows an adjunction to the device in FIG. 1, enabling the studying of the reaction of diverse substances under the effect of the impact produced by high-speed droplets produced by the device according to the invention.

A sample 7 to be studied is placed in the test container 8 arranged in the extension of the chamber 1. It is borne by the plate 9 driven by the motor 10 whose shaft, which is eccentric in relation to the axis of the injector, makes it possible to define accurately a ring of impacts of the droplets. The discharging of the liquid is ensured by the tube 11. The test container 8 is put under a partial vacuum by means of a pipe 12 connected to an appropriate vacuum pumping arrangement.

Test container 8 is preferably used when high-speed droplets with a velocity in the neighborhood of 200 meters/second and above are produced. Such high speed droplets emerge into evacuated container 8 in order to avoid disintegration of the jet.

Figure 3:
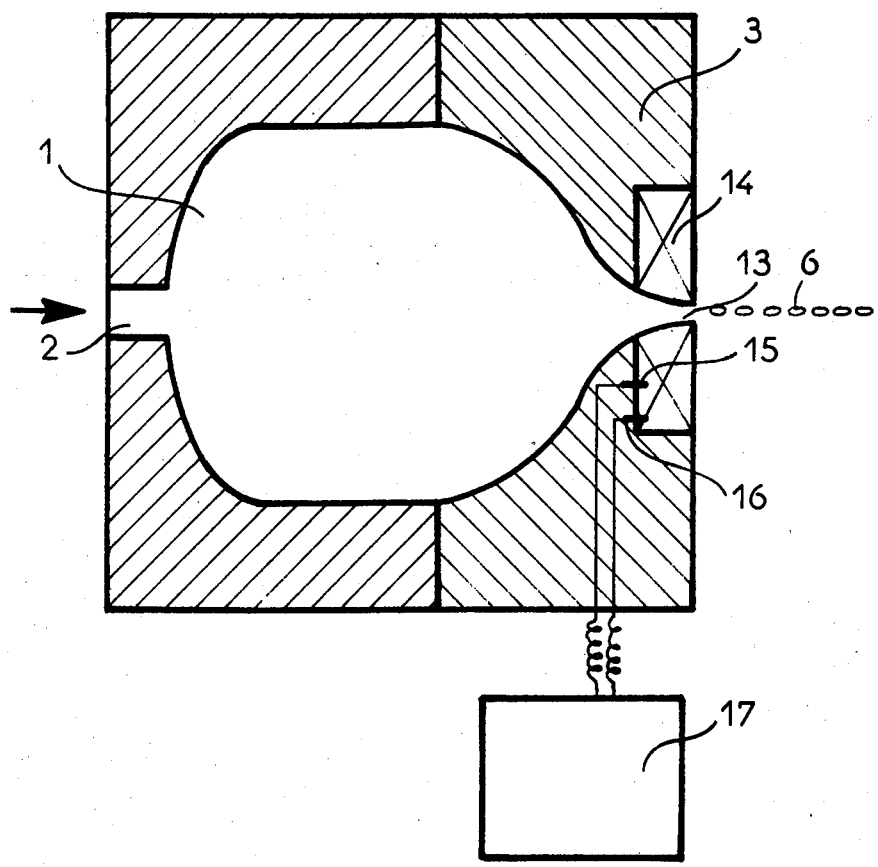
FIG. 3 is a variation of the embodiment of a device according to the invention.

The variation in FIG. 3 shows a device comprising a chamber 1 supplied with liquid under high pressure by a pump, connected to the orifice 2, that chamber ending in an interchangeable injector 3 intended for providing a fast jet, that injector being provided, at its output 13, with a magnetostrictive element 14 comprising electrodes 15 and 16 connected to a high-frequency pulse generator 17, which thus sets the magnetostrictive element vibrating.

That arrangement makes it possible to divide the jet which comes from the orifice 13 in droplets 6 whose dimensions depend on the frequency of the generator 17.

Figure 4:
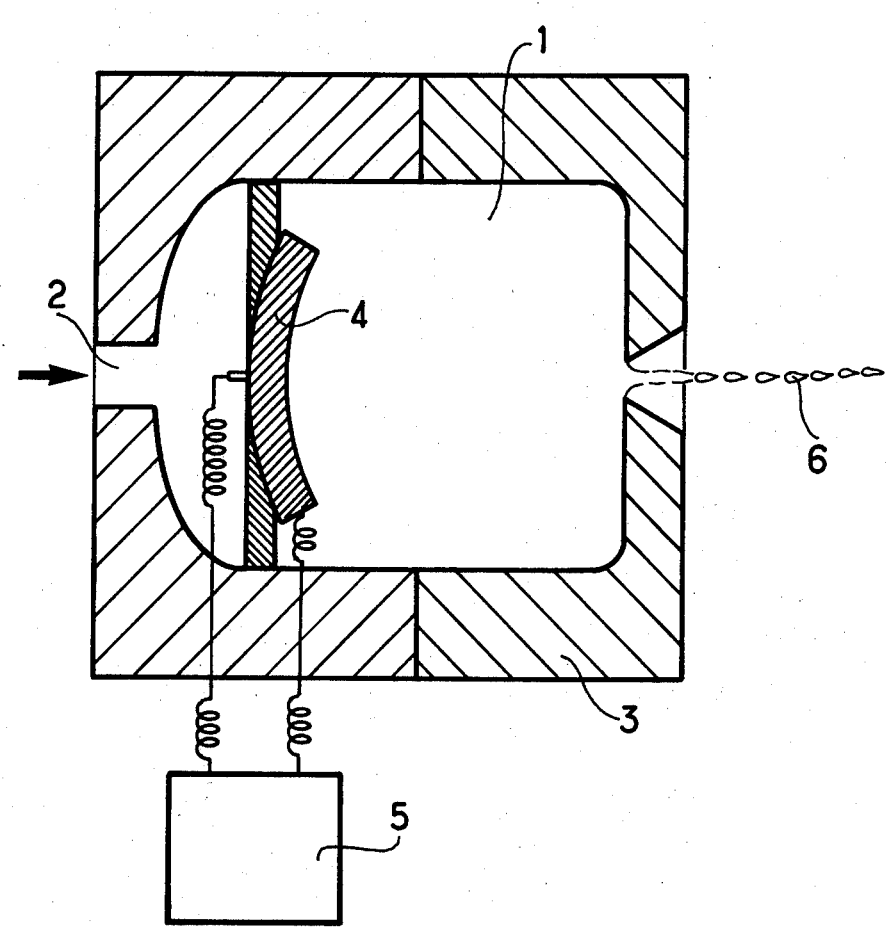
FIG. 4 is an axial cross-sectional view of another variation of the device according to the invention, including a cylindrically shaped chamber with its interior wall through which the output orifice passes being perpendicular to the jet axis and an output orifice with outwardly diverging sides when seen in axial cross-section as depicted in the figure.
Figure 5:
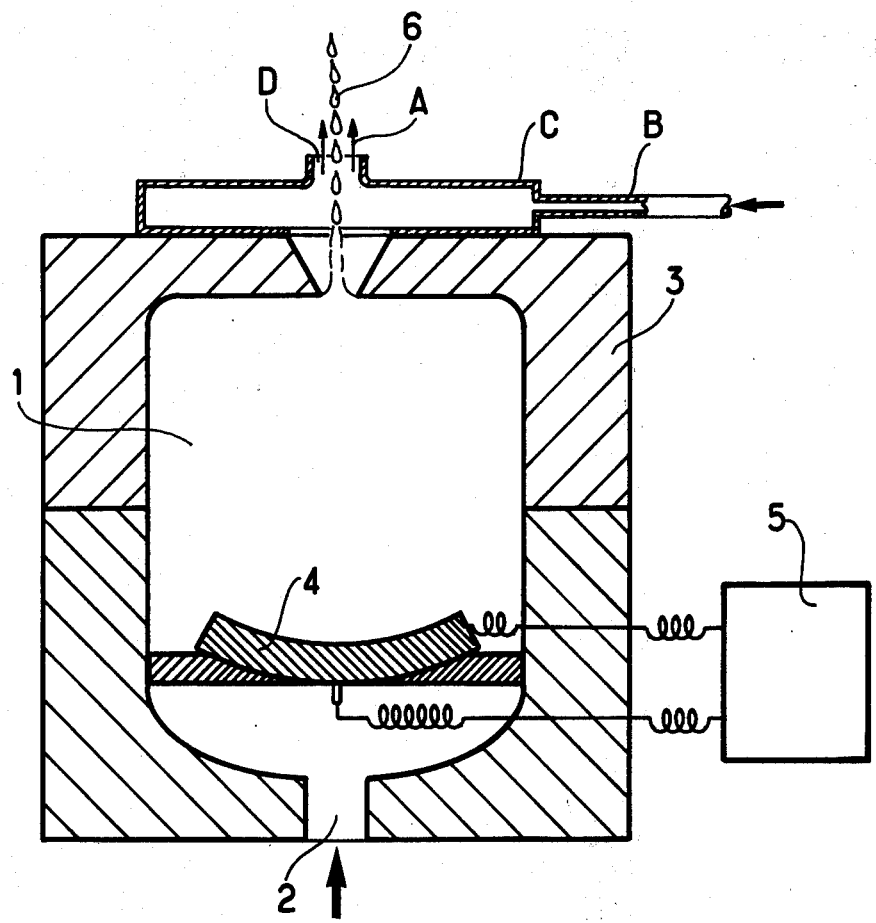
FIG. 5 is an axial cross-sectional view of yet another variation of the device according to the invention.
Figure 6:
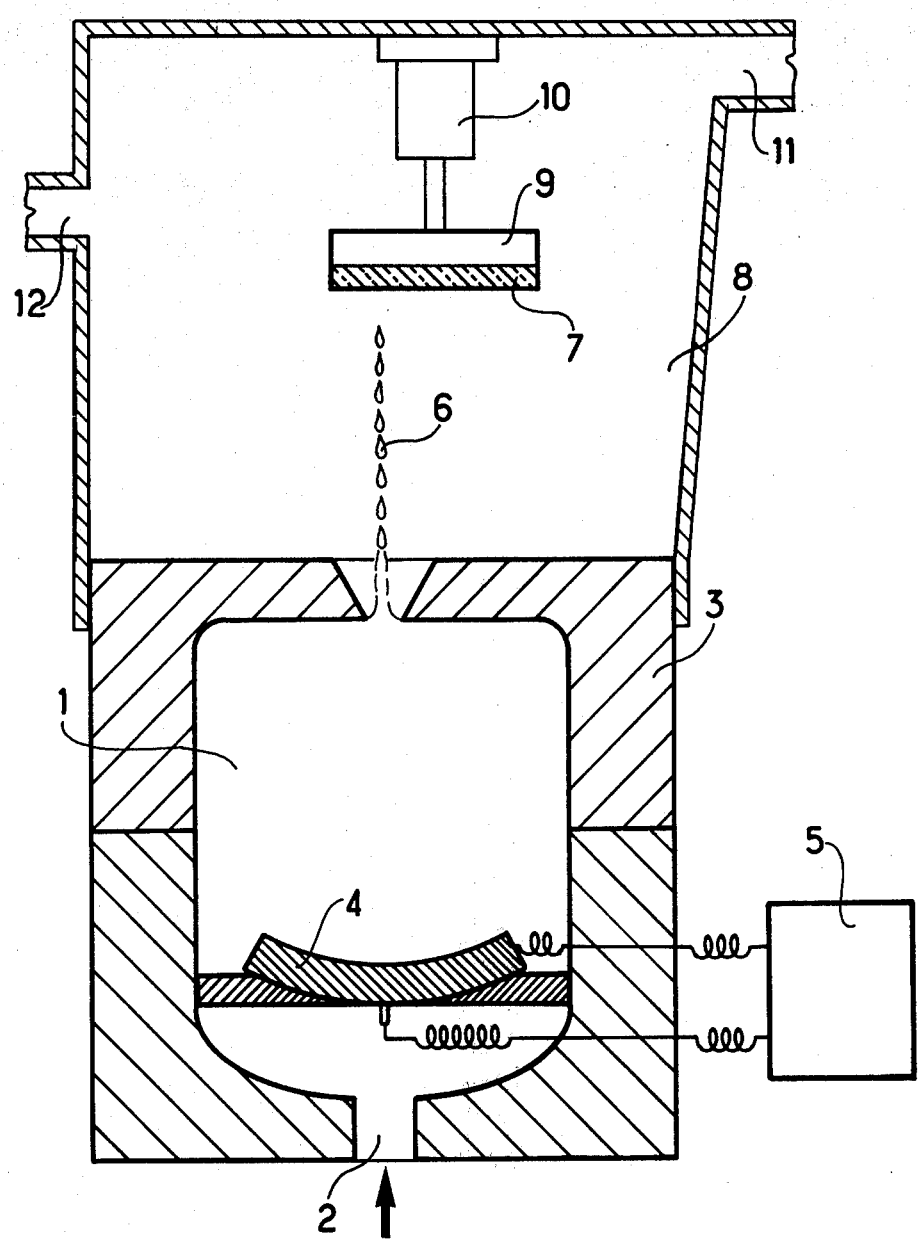
FIG. 6 is an axial cross-sectional view of the device in FIG. 4, arranged for studying a sample.
Figure 7:
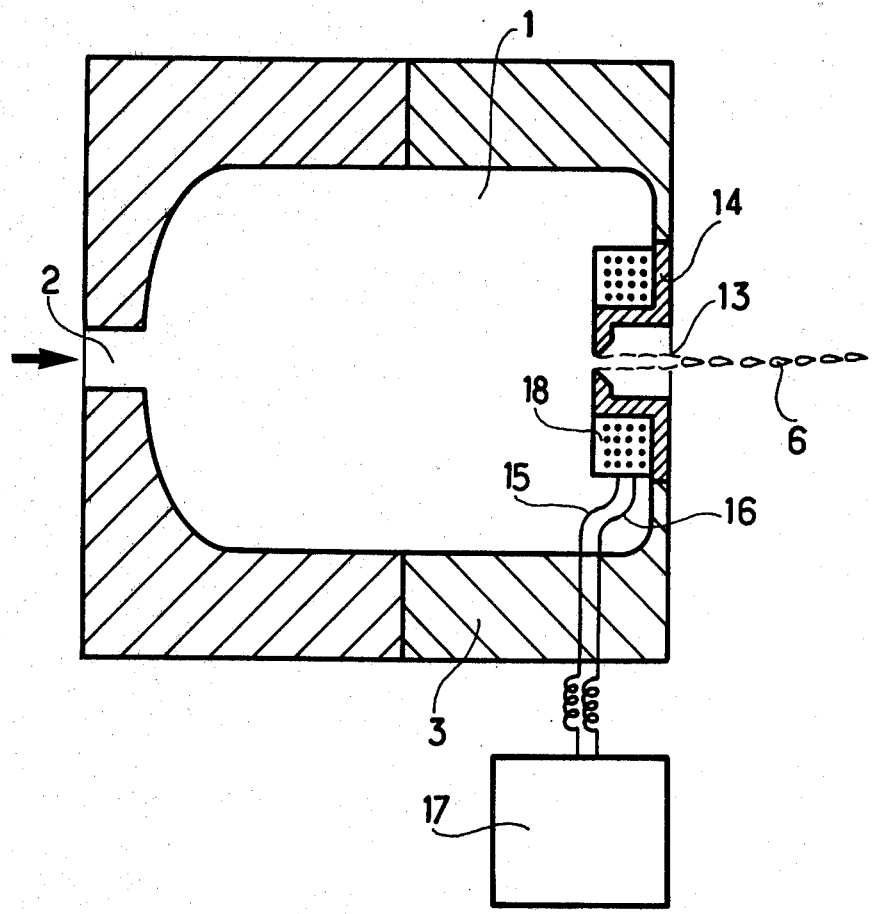
FIG. 7 is an axial cross-sectional view of still another variation of the device according to the invention.

FIG. 4 depicts an embodiment of the invention in which chamber 1 is of cylindrical shape, the longitudinal axis of the cylinder being parallel to and in line with both orifice 2 and the jet of droplets 6.

Since the invention provides drops having a velocity in the range of 100 meters/second at 750 psi to 600 meters/second at 3000 psi, it has been determined that to avoid turbulence which would disintegrte the jet and to provide proper control of both the size and velocity of the jet of droplets, the output orifice of chamber 1 and the chamber should take the shape depicted in FIG. 4.

As illustrated in FIG. 4, the chamber is cylndrically shaped. Its interior wall through which the output orifice passes is perpendicular to the jet axis. Each of the walls of the chamber, including the vertical inside wall through which the output orifice passes, is of sufficient thickness to withstand the high pressures existent within the chamber, these high pressures being in the neighborhood of 750 psi and greater. The output orifice is thin-lipped and has outwardly diverging sides when seen in axial cross-section as depicted in the figure. The output orifice forms a reverse taper toward the exterior side of the chamber such that it is narrower at the interior side of the wall through which it passes than at the exterior side of the injector, as depicted in the figure.

An output orifice taking the particular shape depicted in FIG. 4 enables the device to avoid any undesirable turbulent action which might otherwise be caused by the orifice wall. Additionally, this particular output orifice shape permits a suitable distribution of velocity in the interior of the jet. In order to obtain the thin-lip of the output orifice, the orifice is outwardly tapered toward the exterior of the chamber, as previously described.

In the embodiment depicted in FIG. 4, in order to provide a jet of droplets having velocity in the neighborhood of 100 meters/second, for example, while maintaining in low liquid velocity within the chamber to prevent undesirable turbulence, the diameter of the chamber can be 20 mm. To provide a jet of droplets having velocity in the range of 100 meters/second to 600 meters/second, for example, and still maintain low liquid velocity within the chamber to prevent undesirable turbulence, the diameter of the chamber can be 300 mm. The length of the chamber for these various values would fall in the range of 80 mm to 300 mm.

The relationships between the diameter of the nozzle, the velocity of the jet and the frequency of the vibration can be expressed by the formula:

$$N = \frac{0.12\ V}{\phi}$$

where $N$ is the frequency of the vibrations in Khz, $V$ is the velocity of the jet of droplets in meters/second, and $\phi$ is the diameter of the nozzle in millimeters.

In the embodiment of the invention depicted in FIG. 4, just as in the FIG. 1 embodiment, orifice 2 of chamber 1 can be either a single inlet or plural inlets, but should be parallel to the longitudinal axis of the chamber as depicted in the figure in order to avoid turbulence in the chamber such as that caused by rotation of the liquid therein, and to enable proper control of a coherent jet of droplets.

FIG. 5 illustrates apparatus which insures the avoidance of premature disintegration of the jet of droplets by providing a concentric jet of air or gas A surrounding the drops which has the same high velocity as that of the drops. Jet A is formed by introducing air or gas into chamber C of circular shape, for example, via pipe B. Chamber C has an outlet D through which the jet A of air or gas surrounding the drops 6 is forced to move axially and outwardly at the same high velocity as the drops 6 in order to protect the drops 6 from premature disintegration.

Although the apparatus for protecting the jet of droplets from premature disintegration has specifically been illustrated with an embodiment of the invention as depicted in FIG. 4, the apparatus for protecting the drops can also be used with each of the other disclosed embodiments to obtain the same beneficial results.

Since the device is often used to produce a jet of droplets having velocity in the neighborhood of 200 meters/second and above, vacuum chamber 8 illustrated in FIG. 6 is provided to avoid disintegration of the jet. FIG. 6 shows the invention including test container 8 disposed adjacent injector 3 where a cylindrical chamber 1 having its interior wall through which the output orifice passes being perpendicular to the jet axis and thin-lipped outlet orifice forming a reverse taper toward the exterior side of the chamber are included; however, test container 8 can be used with each of the other disclosed embodiments of the invention in order to obtain similar beneficial results.

FIG. 7 depicts another embodiment of the device which permits the jet of droplets 6 emitted from orifice 13 to have dimensions dependent upon the frequency of generator 17. In this embodiment, magnetostrictive element 14 is surrounded by electric coil 18 which is connected through electrodes 15 and 16 to high frequency generator 17 for vibrating magnetostrictive element 14. Chamber 1 can take a cylindrical shape and have its interior wall through which the droplets pass being perpendicular to the axis of the jet as illustrated, and orifice 13 as depicted in the figure can be thin-lipped and reverse tapered toward the exterior of the chamber.

While I have shown and described only several embodiments in accordance with the present invention, it is understood that the same is not limited thereof but is susceptible of numerous changes and modifications as known to those skilled in the art. For example, although chamber 1 was depicted as being of cylindrical shape in only several embodiments of the invention, the chamber in the other embodiments could also assume the same shape. Similarly, although the outlet orifice has only been shown in several embodiments as forming a reverse taper toward the exterior side of the chamber such that it is narrower at the interior side of the wall through which it passes than at the exterior side of the injector, the orifice in the other embodiments could also assume the same shape to obtain the same beneficial results. Similar comments apply to the disclosed apparatus providing a concentric jet of air or gas surrounding the drops and the vacuum chamber 8. I therefore do not wish to be limited to the details shown and described herein, but intend to cover all such changes and modificatins as are encompassed by the scope of the appended claims.

I claim:

1. A method of forming a very fast succession of identical and well-defined drops driven at a very high speed, comprising the steps of supplying a liquid under very high pressure of approximately 750 psi or greater to the inlet of a high pressure chamber, generating a very high speed jet of liquid under very high static pressure at the outlet of said high pressure chamber, and dividing said very high speed jet of liquid into a stream of drops by the application of high-frequency vibration at high power in a direction along the path of said jet of liquid.

2. A method s defined in claim 1, wherein the step of generating includes generating a jet having a speed of approximately 100 meters/second or greater.

3. A method as defined in claim 1, wherein the step of dividing includes applying high-frequency vibration of approximately 200Kc/s or greater.

4. A method as defined in claim 1, further comprising the step of applying the well-defined drops driven at very high speed to a surface for at least one of cleaning, cutting and drilling holes therein.

5. A method as defined in claim 1, wherein the high pressure is in the range of 750 psi to 3,000 psi.

6. A device for forming a very fast succession of identical and well-defined drops at a very high speed, comprising a high pressure chamber; means for supplying said chamber with liquid under high pressure of approximately 750 psi or greater, means for generating a high speed jet including one wall of said chamber forming an injector nozzle capable of providing a fast jet; and ultrasonic generator means for generating a high-frequency field focused at a given point in said liquid on the level of the origin of said jet.

7. device according to claim 6, wherein said generating means generates a jet having a very high speed of approximately 100 meters/second or greater.

8. A device according to claim 6, wherein said generating means generates a high-frequency field of approximately 200 Kc/s or greater.

9. device according to claim 6, wherein said ultrasonic generator means is situated in said chamber upstream from said injector.

10. A device according to claim 6, wherein said ultrasonic generator means comprises a generator producing a field whose wavelength is equal to the diameter of said injector nozzle.

11. A device according to claim 6, wherein said injector nozzle forms a reverse taper towards the exterior of said chamber in the direction of the path of said drops, said nozzle being wider at the exterior of said chamber than at the interior thereof.

12. A device according to claim 11, wherein said chamber is in the shape of a cylinder, the longitudinal axis of said cylinder being parallel to said path of said drops.

13. A device according to claim 12, wherein the wall of said cylinder through which said jet passes is perpendicular to said path of said drops.

14. A device according to claim 6, further including a container surrounding said injector nozzle and into which said drops enter, said container being kept at the vapor pressure of the liquid used and a sample disposed in said container to which said drops are directed.

15. A device according to claim 6, wherein said high pressure chamber is provided with at least one orifice disposed parallel to the longitudinal axis of the chamber and said means for supplying said chamber with liquid under high pressure supplies the liquid therethrough.

16. A device for forming a very fast succession of identical and well-defined drops at a very high speed, comprising a high pressure chamber; means for supplying said chamber with liquid under high pressure, one wall of said chamber forming an injector nozzle capable of providing a fast jet; and ultrasonic generator means for generating a high-frequency field focused at a given point in said liquid on the level of the origin of said jet; and further including at the output of said injector nozzle, means for supplying gas surrounding said drops and having the same speed as said drops.

17. A device for forming a very fast succession of identical and well-defined drops at a very high speed comprising a chamber supplied with liquid under very high pressure of approximately 750 psi or greater, means for generating a jet including one wall of said chamber forming an injector nozzle means for supplying a fast jet, said injector nozzle means being provided with means for generating an ultrasonic vibration along the axis of said injector nozzle means provided in the form of a magnetrostrictive element in surrounding relation thereto and connected to a source of high frequency.

18. A device according to claim 17, wherein said generating means generates a jet having a very high speed of approximately 100 meters/second or greater.

19. A device according to claim 17, wherein said source of high frequency provides a high-frequency of approximately 200 Kc/s or greater.

20. A device according to claim 17, wherein said injector nozzle means forms a reverse taper towards the exterior of said chamber in the direction of the path of said drops, said nozzle means being wider at the exterior of said chamber than at the interior thereof.

21. A device according to claim 20, wherein said chamber is in the shape of a cylinder, the longitudinal axis of said cylinder being parallel to said path of said drops.

22. A device according to claim 21, wherein the wall of said cylinder through which said jet passes is perpendicular to said path of said drops.

23. A device according to claim 17, characterized in that it includes, at the output of said injector nozzle means, means for supplying gas surrounding said drops and having the same speed as said drops.

24. A device according to claim 17, further including a container surrounding said injector nozzle means and into which said drops enter, said container being kept at the vapor pressure of the liquid used and a sample disposed in said container to which said drops are directed.

\* \* \* \* \*